(12) United States Patent
Lin et al.

(10) Patent No.: US 10,571,673 B2
(45) Date of Patent: Feb. 25, 2020

(54) PARTICLE POSITIONING DEVICE WITH PERIODIC DIELECTRIC STRUCTURE

(71) Applicant: University of Washington, Seattle, WA (US)

(72) Inventors: Lih-Yuan Lin, Seattle, WA (US); Ethan G. Keeler, Seattle, WA (US)

(73) Assignee: UNIVERSITY OF WASHINGTON, Seattle, WA (US)

( * ) Notice: Subject to any disclaimer, the term of this patent is extended or adjusted under 35 U.S.C. 154(b) by 311 days.

(21) Appl. No.: 15/488,806

(22) Filed: Apr. 17, 2017

(65) Prior Publication Data

US 2017/0299494 A1 Oct. 19, 2017

Related U.S. Application Data (60) Provisional application No. 62/323,405, filed on Apr. 15, 2016.

(51) Int. Cl.
*G02B 21/32* (2006.01)
*G01N 15/10* (2006.01)

(52) U.S. Cl.
CPC ..... *G02B 21/32* (2013.01); *G01N 2015/1006* (2013.01)

(58) Field of Classification Search
CPC .............. G02B 21/32; G01N 15/1459; G01N 15/1484; G01N 15/1434; G01N 2015/0038; G01N 2015/1006
See application file for complete search history.

(56) References Cited

U.S. PATENT DOCUMENTS

| | | | |
|---|---|---|---|
| 5,445,011 A | 8/1995 | Ghislain et al. | |
| 8,087,284 B2 | 1/2012 | Babcock et al. | |
| 8,312,763 B2 | 11/2012 | Manalis et al. | |
| 8,631,685 B2 | 1/2014 | Manalis et al. | |
| 2012/0244532 A1* | 9/2012 | Craighead | B01L 3/502761 435/6.11 |
| 2013/0074586 A1 | 3/2013 | Blanco-Gomez et al. | |

OTHER PUBLICATIONS

Burg et al.; Weighing of Biomolecules, Single Cells and Single Nanoparticles in Fluid; Nature; Apr. 26, 2007; pp. 1066-1069; vol. 446; Nature Publishing Group.

(Continued)

*Primary Examiner* — Michael L Hobbs
(74) *Attorney, Agent, or Firm* — K&L Gates LLP (57) ABSTRACT

Devices and techniques for a particle positioning device are generally described. In some examples, a fluid may be introduced to a channel formed on a first surface of a substrate. In various examples, the channel may comprise a periodic dielectric structure etched in a first surface of the substrate and a channel wall material. In some examples, a laser beam may be directed through the channel wall material to the periodic dielectric structure. In various further examples, the laser beam may be reflected from the periodic dielectric structure into an interior region of the channel to form a focal enhancement region of the laser beam in the interior region of the channel adjacent to the periodic dielectric structure. In various examples, a force may be exerted on a particle suspended in the fluid with an electric field gradient generated by the focal enhancement region of the laser beam.

19 Claims, 10 Drawing Sheets

(56) References Cited

OTHER PUBLICATIONS

Barton et al.; Fabrication of a Nanomechanical Mass Sensor Containing a Nanofluidic Channel; NANO Letters; May 5, 2010; pp. 2058-2063; vol. 10; American Chemical Society.

Younis et al.; A Reduced-Order Model for Electrically Actuated Microbeam-Based MEMS; Journal of Micromechanical Systems; Oct. 2013; pp. 672-680; vol. 12 , No. 5.

Jing et al.; Patterned Optical Trapping with Two-Dimensional Photonic Crystals; ACS Photonics; Apr. 14, 2014; pp. 398-402; ACS Publications.

Gibson; Optical Resonant Frequency Detection System for Mass-Sensing MEMS Resonators; NNIN REU Research Accomplishments; 2015; pp. 140-141; University of Washington; Seattle, WA.

Younis et al; A Reduced-Order Model for Electrically Actuated Microbeam-Based MEMS; Journal of Microelectromechanical Systems; Oct. 2003; pp. 672-680; vol. 12; No. 5.

Neuman et al.; Optical Trapping; AIP Review of Scientific Instruments; Sep. 2, 2004; pp. 2787-2809; vol. 75; No. 9.

Davila et al.; Microresonator Mass Sensors of Detection of Bacillus Anthracis Sterne Spores in Air and Water; Biosensors and Bioelectronics; Jan. 25, 2007; pp. 3028-3035; vol. 22; Issue 12.

Burg et al.; Weighing of Biomolecules, Single Cells and Single Nanoparticles in Fluid; Nature Letters; Apr. 26, 2007; pp. 1066-1069; vol. 446.

Park et al.; 'Living Cantilever Arrays' for Characterization of Mass of Single Live Cells in Fluids; Lab on a Chip; Jun. 2008; pp. 993-1228; vol. 8; Issue 7.

Mandal et al.; Nanomanipulation Using Silicon Photonic Crystal Resonators; Nano Letters; Dec. 2, 2009; pp. 99-104; vol. 10.

Barton et al.; Fabrication of a Nanomechanical Mass Sensor Containing a Nanofluidic Channel; Nano Letters; May 5, 2010; pp. 2058-2063; vol. 10.

Park et al.; Measurement of Adherent Cell Mass and Growth; Proceedings of the National Academy of Sciences; Nov. 10, 2010; pp. 20691-20696; vol. 107; Issue 48.

Boisen et al.; Cantilever-Like Micromechanical Sensors; Reports on Progress in Physics; 2011; 31 pgs; vol. 74; Issue 3.

Wasisto et al.; Determination of Exposure to Engineered Carbon Nanoparticles Using a Self-Sensing Piezoresistive Silicon Cantilever Sensor; Microsystem Technologies; Jan. 6, 2012; pp. 905-915; vol. 18.

Jing et al.; Patterned Optical Trapping with Two-Dimensional Photonic Crystals; ACS Photonics; Apr. 14, 2014; pp. 398-402; vol. 1.

Gibson et al.; Optical Resonant Frequency Detection System for Mass-Sensing MEMS Resonators; Optics and Opto-Electronics; 2015; 2 pgs.

Keeler et al; MEMS Resonator and Photonic Crystal Integration for Enhanced Cellular Mass Sensing; Optics in the Life Sciences; 2015; 3 pgs.

\* cited by examiner

PARTICLE POSITIONING DEVICE WITH PERIODIC DIELECTRIC STRUCTURE

CROSS-REFERENCE TO RELATED APPLICATIONS

This application claims the benefit of U.S. Provisional Application No. 62/323,405, filed Apr. 15, 2016, the disclosure of which is incorporated herein by reference in its entirety.

STATEMENT OF GOVERNMENT LICENSE RIGHTS

This invention was made with government support under Grant No. DBI-1353718, awarded by the National Science Foundation. The government has certain rights in the invention.

FIELD

This application relates to analysis of small particles and in some cases living cells and/or biomolecules.

BACKGROUND

Various devices have been developed to study the characteristics of small (e.g., micro- and nano-sized) particles, including living cells. Physical properties of cells, such as cell mass, may be used to study cell growth rate and cell cycle progression which, in turn, may be used to evaluate therapeutics, disease progression, etc. Additionally, devices have been developed to study the properties of small non-cellular particles. Due to the small size of such particles, it may be difficult to isolate the particles in order to subject the particles to various analysis techniques. Additionally, living cells may be suspended in fluidic channels, which introduce variability into analysis techniques due to motion of the particles within the fluidic channel.

SUMMARY

In various examples, systems and methods are provided for particle analysis devices including periodic dielectric structures.

In accordance with some embodiments of the present invention, particle positioning systems are generally described. In various examples, the systems may comprise a laser light source configured to emit a laser beam. In some further examples, the systems may comprise a particle positioning structure. In various examples, the particle positioning structure may comprise a substrate. In some examples, a first surface of the substrate may include a periodic dielectric structure. In various other examples, the particle positioning structure may comprise a channel wall material coupled to the substrate such that the channel wall material forms a channel adjacent to the periodic dielectric structure. In further examples, the channel wall material may be at least partially optically transparent to the laser beam from the laser light source. In various other examples, the laser light source may be adapted to direct the laser beam through the channel wall material and through an interior region of the channel to the periodic dielectric structure. In some examples, the laser beam may be reflected by the periodic dielectric structure into the interior region of the channel.

In accordance with some other embodiments of the present invention, methods of positioning particles are generally described. In various examples, the methods may include introducing a fluid to a channel formed on a first surface of a substrate. In some examples, the channel may comprise a periodic dielectric structure etched in a first surface of the substrate and a channel wall material. In various further examples, the methods may include directing a laser beam through the channel wall material to the periodic dielectric structure. In some further examples, the methods may further comprise reflecting the laser beam from the periodic dielectric structure into an interior region of the channel to form a focal enhancement region of the laser beam in the interior region of the channel adjacent to the periodic dielectric structure. In various other examples, the methods may further comprise exerting a force on a particle suspended in the fluid with an electric field gradient generated by the focal enhancement region of the laser beam.

In some other embodiments of the present disclosure, methods of fabricating a particle positioning structure are generally described. In at least some examples, the methods may comprise etching a first surface of a substrate to form a periodic dielectric structure in the first surface of the substrate. In some further examples, the methods may comprise coupling a patterned photoresist to the periodic dielectric structure. In still further examples, the methods may comprise depositing a parylene layer on the first surface of the substrate and on an exposed surface of the patterned photoresist. In various other examples, the methods may further comprise releasing the patterned photoresist using a solvent to form a channel between the parylene layer and the periodic dielectric structure.

Still other embodiments of the present invention will become readily apparent to those skilled in the art from the following detailed description, wherein are described embodiments by way of illustrating the best mode contemplated for carrying out the invention. As will be realized, the invention is capable of other and different embodiments and its several details are capable of modifications in various obvious respects, all without departing from the spirit and the scope of the present invention. Accordingly, the drawings and detailed description are to be regarded as illustrative in nature and not as restrictive.

DETAILED DESCRIPTION

In the following description, reference is made to the accompanying drawings that illustrate several embodiments of the present disclosure. It is to be understood that other embodiments may be utilized and system or process changes may be made without departing from the spirit and scope of the present disclosure. The following detailed description is not to be taken in a limiting sense, and the scope of the embodiments of the present invention is defined only by the claims of the issued patent. It is to be understood that drawings are not necessarily drawn to scale.

Various embodiments of the present disclosure provide improved systems and methods for micro-scale and nano-scale particle analysis. Small particles, such as nanoscale particles (e.g., 1-1000 nanometers in diameter and/or other dimension) and/or microscale particles (e.g., from 1-1000 micrometers in diameter and/or other dimension), may be difficult to analyze using conventional methodologies due to the elusive size scale of the particles. Use of conventional analysis methodologies may lead to introduction of significant noise into results due to the small mass and sizes of micro and nano-scale particles. Additionally, in some examples, bio-molecules, such as cells, may require a fluidic channel in order to keep the biomolecules from dying and/or otherwise degrading. A fluidic channel in which small particles are suspended may introduce further complexities when attempting to study properties of the particles due to the highly complex fluid environment and uncertain trajectory of particles within the fluid. Accordingly, the devices and techniques described herein provide methodologies for conveying and positioning sample particles and cells for analysis. Additionally, various devices and techniques described herein may be effective to prevent cell death and/or degradation due to photodamage while conveying and/or positioning living cells in a fluidic environment.

In some examples, micro-electro-mechanical systems (MEMS) resonators may be used to analyze particles, including bio-molecules and cells as well as inorganic particles. The term "particles", as used herein, may comprise one or more of organic material, inorganic material, biological molecules, and/or cells. MEMS resonators, in various configurations, provide a sensitive platform that may be used to detect information about various mechanical properties of particles including mass, density, size, and/or stiffness. For living cells, information about cell mass, density, size and/or stiffness may allow for analysis of cell growth, transformation, and morphology.

MEMS resonators may use a resonant actuation mechanism that can accommodate adherent or suspended particles. By observing the change in resonant frequency of these structures due to the presence of the adherent or suspended particles, properties such as mass, density, size, and/or stiffness may be determined. Cantilever or pedestal structures are often employed for actuation as MEMS resonators. In some other examples, a fixed-fixed beam, bridge-like structure may be used to simplify any potentially required fluidic geometry. An electrode or conductive, doped layer may be used as an actuation mechanism to induce resonant, electrostatic actuation of the structure.

Variability in particle position during resonant actuation of the structures introduces noise into the analysis. Noise due to variance in particle positioning is particularly problematic in scenarios where particles, such as living cells, are suspended in a microfluidic channel. Mechanical trapping of particles requires physical interaction with the particles, which can result in measurement degradation and external perturbation to the cell or other particle. Further, mechanical trapping may offer only temporary trapping of particles suspended in solution, as the particles can eventually flow out of the traps. As an alternative, optical trapping may have a number of key advantages: it may achieve excellent trap precision; it may be adaptable and reconfigurable with dynamic trapping control; and it may be a "contactless" capture modality without the need for mechanical mediation.

Figure 1:
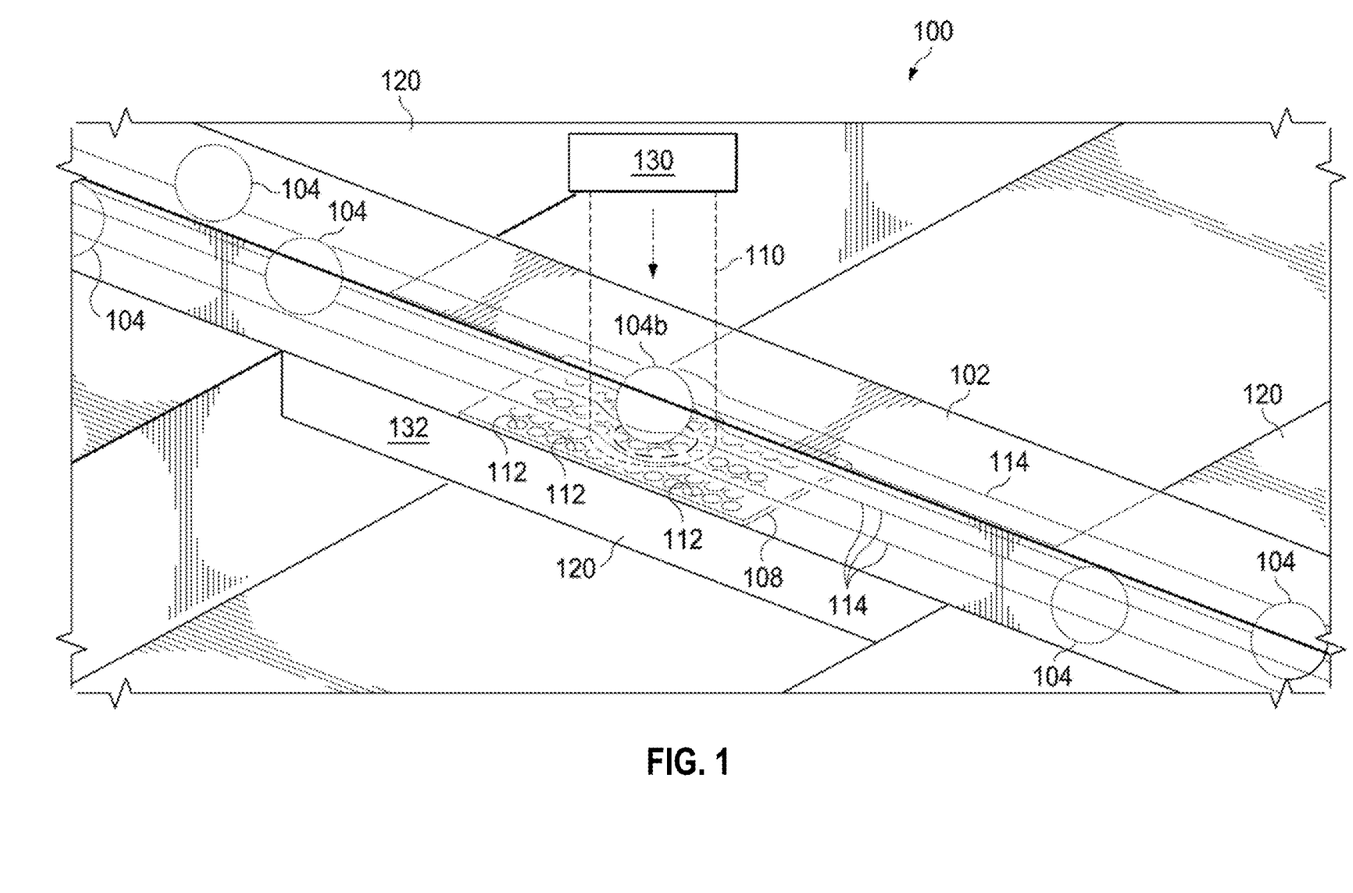
FIG. 1 depicts a particle positioning structure including a periodic dielectric structure, in accordance with various embodiments of the present disclosure.

FIG. 1 depicts a particle positioning structure 100 including a channel 102. Channel 102 may comprise a hollow, tunnel-like structure. In various examples, channel 102 may be a fluidic channel through which a fluid may pass. Particles 104 may be introduced into channel 102. In examples where channel 102 is a fluidic channel, particles 104 may be suspended in a fluid within channel 102. In some examples, fluid within channel 102 may be used to convey particles 104 through channel 102, as indicated by flow-lines 114. In some examples, channel 102 and/or portions of channel 102 may be formed from a channel wall material that is at least partially optically transparent to laser light. For example, channel 102 and/or portions of channel 102 may be formed from a material that transmits a desired range of wavelengths of light. In various examples, channel 102 may be formed on a substrate 120. Techniques for formation of channel 102 and, more generally, particle positioning structure 100, are described in further detail below.

Particle positioning structure 100 may include a periodic dielectric structure 108. The term "periodic dielectric", as used herein, may refer to two-dimension, periodic surface structuring to achieve diffractive modulation of an impinging laser beam. In some examples, periodic dielectric structure 108 may comprise a number of holes 112 arranged in a periodic manner. Holes 112 may be formed by etching a surface of substrate 120. In various examples, holes 112 may not extend through substrate 120 to another surface of substrate 120 to form a channel through substrate 120. Accordingly, holes 112 may represent divots and/or depressions formed in a surface of substrate 120 by etching away portions of the surface of substrate 120 to a desired depth. In examples where substrate 120 is a silicon substrate, holes 112 of periodic dielectric structure 108 may be formed by etching a surface of the silicon to form a desired periodic structure. Various parameters of periodic dielectric structure 108 may be altered according to desired applications of particle positioning structure 100. Examples of parameters of periodic dielectric structure 108 that may be altered include the periodicity of holes 112, the dimensions of individual holes 112, the depth of holes 112, the shape of holes 112 (e.g., hexagonal, square, circular, diamond, etc.), and the pattern/configuration of holes 112. In some examples, and as described in further detail below, the aforementioned parameters of periodic dielectric structure 108 may be altered in order to optimize particle positioning structure 100 for positioning of a particular particle type (e.g., a mammalian cell), depending on characteristics of the particular particle (e.g., size).

In some examples, periodic dielectric structure 108 may form a lower side of, or a portion of a lower side of channel 102. In some other examples, an at least partially optically clear channel 102 may be formed on top of periodic dielectric structure 108 such that light may pass between an interior region of channel 102 and an upper surface of periodic dielectric structure 108. In various examples, a laser light source 130 may be effective to direct laser light 110 (e.g., a laser beam) through channel 102. In some examples, a Nd:YVO$_4$ (1064 nanometer wavelength) laser may be used. Depending on the type of and configuration of the external optical system used, a relatively low-intensity laser may be used for optical trapping in order to avoid optical damage to the particles being held in position using particle positioning structure 100. For example, an intensity of the laser light source 130 may be ≤100 µW/µm$^2$ at the focus region of a microscope used to observe the particle 104b or other regions of channel 102.

The laser light 110 may be reflected by the periodic dielectric structure 108 and may be effective to form an optical trap (sometimes referred to as "optical tweezers") to hold a particle in position. A focal region (sometimes referred to as the "beam waist") of the laser light reflected by the periodic dielectric structure 108 may produce an electric field gradient that may attract dielectric particles. Accordingly, the laser light emitted by the laser light source 130 and reflected by the periodic dielectric structure 108 may form an optical trap effective to hold particles passing through channel 102 in position. This modulated optical trap is intentionally coupled to the resonant vibrations in surface of substrate 120. Various analysis techniques, such as the MEMS resonant mass-sensing techniques described herein may be performed on the trapped particle. In the depiction in FIG. 1, particle 104b, is trapped in the optical trap of particle positioning structure 100. Additionally, the optical trap may be used to sort and/or separate particles passing through channel 102.

As previously described, in some examples particle positioning structure 100 may comprise and/or may be coupled to a MEMS resonator in order to produce a resonant, electrostatic actuation of the structure 132 upon which channel 102 is formed, as depicted in FIG. 1. Although structure 132 is depicted as a beam-shaped structure in FIG. 1, in various other examples, structure 132 may be a cantilever, pedestal, or other-shaped structure. The shape of structure 132 may in some cases facilitate resonant actuation of the structure 132. An external electrode may be coupled to the structure 132 to facilitate and induce the resonant actuation of the structure 132. In the example of a doubly-clamped (fixed-fixed) implementation, the electrostatically driven response of the beam may be governed by the non-dimensional differential relationship shown in Eq. (1) where w(x, t) is the normalized transverse deflection along the beam, v(t) is the actuation voltage, and c, $\alpha_1$, $\alpha_2$, and N are parameters that consider damping, material properties, dimensions, and loading of the structure 132.

$$\frac{\partial^4 w}{\partial x^4} + \frac{\partial^2 w}{\partial t^2} + c\frac{\partial w}{\partial t} = [\alpha_1 \Gamma(w, w) + N] \times \frac{\partial^2 w}{\partial x^2} + \frac{\alpha_2 v^2(t)}{(1-w)^2} \quad (1)$$

where $$\Gamma(f_1(x, t), f_2(x, t)) = \int_0^1 \frac{\partial f_1}{\partial x} \frac{\partial f_2}{\partial x} dx$$

Differential equation (1) is subject to the following boundary conditions (M. I. Younis, E. M. Abdel-Rahman, and A. Nayfeh, "A Reduced-Order Model for Electrically Actuated Microbeam-based MEMS," J. Microelectromechanical Sys. 12(5), 672-680 (2003)):

$$w(0, t) = w(1, t) = 0 \quad (2)$$
$$\frac{\partial w}{\partial x}(0, t) = \frac{\partial w}{\partial x}(1, t) = 0$$

In addition to determination of the resonant frequency and damping characteristics, by reducing the forcing voltage to only a static component and setting the time derivative to zero, the resulting static solution may aid in determining the structure 132 dimensions and electrode spacing. To further refine the parameters of structure 132, simulations revealed the resonant frequency in one embodiment of the beam structure (structure 132 in FIG. 1 including channel 102) to lie in the 200 kHz range for a beam structure 25 µm by 2 µm with lengths ranging around 250 to 300 µm and a channel cross-section of approximately 10 µm by 7 µm with 5-µm thick walls. To achieve measurable beam structure deflection, the spacing between the beam structure and electrode may be approximately 5 µm. With a thinner beam structure, the actuation voltage can be reduced and/or the separation between the beam structure and the electrode can be increased to lessen external structural damping. Additionally, the overall resonator mass can be minimized in view of sensitivity considerations.

Figure 2:
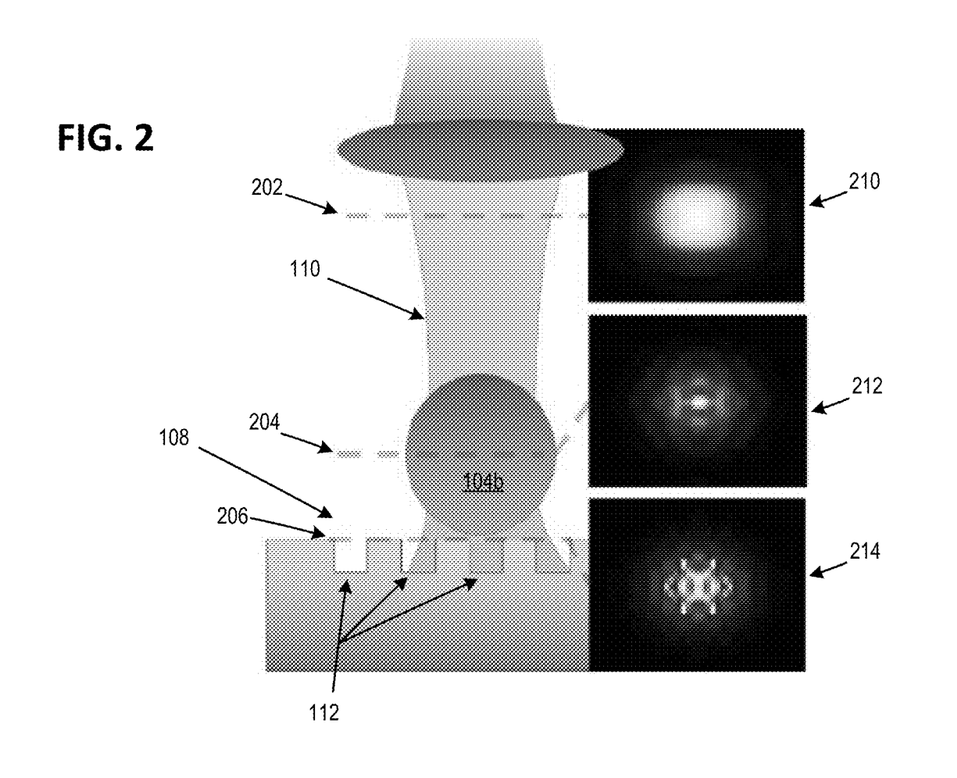
FIG. 2 illustrates an optical trap including a periodic dielectric structure used to hold a particle in position, in accordance with various embodiments of the present disclosure.

FIG. 2 depicts an optical trap including a periodic dielectric structure 108, used to hold a particle 104b in position, in accordance with various embodiments of the present disclosure. Images 210, 212, and 214 depict representations of the focal intensity of laser light 110 at focal planes 202, 204, and 206, respectively. As shown in image 212, a focal enhancement region occurs just above the periodic dielectric structure 108 at focal plane 204, as determined by hole depth and feature geometry. The trapping phenomenon arises from inhomogeneity in the electromagnetic field produced by the focal enhancement region of the laser light 110. The electromagnetic field gradient exerts a force on dielectric particles. Dielectric particles are attracted along the gradient to the region of strongest electric field (e.g., at the center of the beam waist). The periodic dielectric structure 108 affects the electromagnetic field gradient and the focal enhancement region and increases the optical trapping force for a given optical power of the laser light 110. Accordingly, using the periodic dielectric structure 108 to at least partially focus laser light 110 allows for a reduction in overall optical power for a given trapping force. Accordingly, the use of the periodic dielectric structure 108 in optical traps and tweezers may be particularly beneficial for trapping living cells which may otherwise suffer opticution (damage beyond viability through photodamage) when subjected to high powered laser light. Additionally, using the diffraction properties of the periodic dielectric structure 108 may ensure that the trapped particle is always positioned on the surface of the periodic dielectric structure 108, allowing the trapped particle to resonate with the silicon beam structure 132, satisfying a necessary condition of resonant mass sensing for those embodiments of particle positioning structure 100 including or coupled to a MEMS resonator.

Various parameters of periodic dielectric structure 108 may be altered in order to optimize the focal enhancement region of the laser light (e.g., the narrowest point of the beam waist) to position particular types of particles. For example, the periodicity of holes 112, the dimensions of individual holes 112, the depth of holes 112, the shape of holes 112

(e.g., hexagonal, square, circular, diamond, etc.) the pattern of holes 112, etc. may be altered to adjust the position of the focal enhancement region (e.g., the position of the beam waist) with respect to the surface of the periodic dielectric structure 108, depending on the size of the particle to be held in position with the optical trap. For example, the parameters of periodic dielectric structure 108 may be altered to raise or lower focal plane 204 in order to position a particle of a particular size. In some examples, a particular focal plane 204 optimized for a particular particle may have a tolerance range of about +/−2-8 microns. In some examples, for positioning submicron particles, focal plane 204 may be lowered using a smaller periodicity and/or smaller sized, deeper holes of periodic dielectric structure 108. In various examples, the distance between holes 112 may be from about 4-8 microns. In various other examples, the depth of holes 112 may be from about 0.1 microns to about 0.5 microns.

FIG. 3 (including FIGS. 3A-3I) depicts various stages of a fabrication process for the particle positioning structure 100 of FIG. 1, in accordance with various embodiments of the present disclosure. Those portions of FIG. 3 that have been previously described with respect to FIGS. 1 and 2 may not be described again in reference to FIG. 3 for purposes of clarity and brevity.

Silicon-on-insulator (SOI) techniques may be used to fabricate a silicon beam, such as structure 132 depicted in FIG. 1 according to known techniques. However, particle positioning structure 100 requires formation of channel 102 passing over a periodic dielectric structure 108.

Figure 3A:
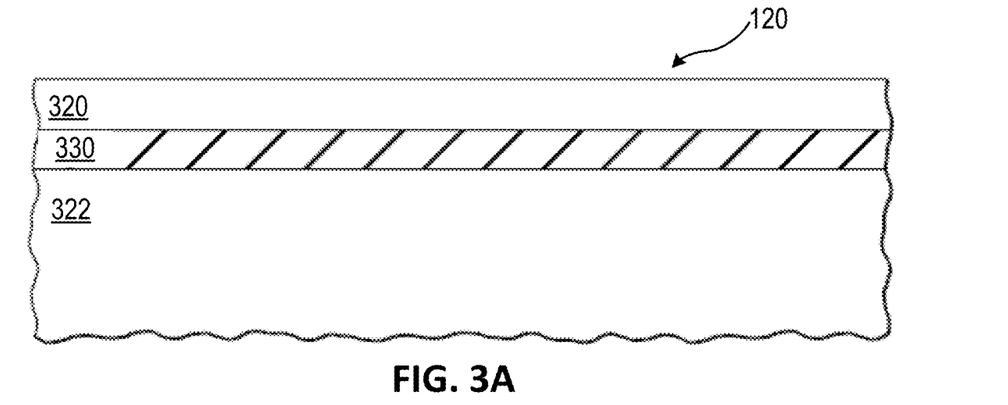
FIGS. 3A-3I depict various stages of a fabrication process for the particle positioning structure of FIG. 1, in accordance with various embodiments of the present disclosure.
Figure 3B:
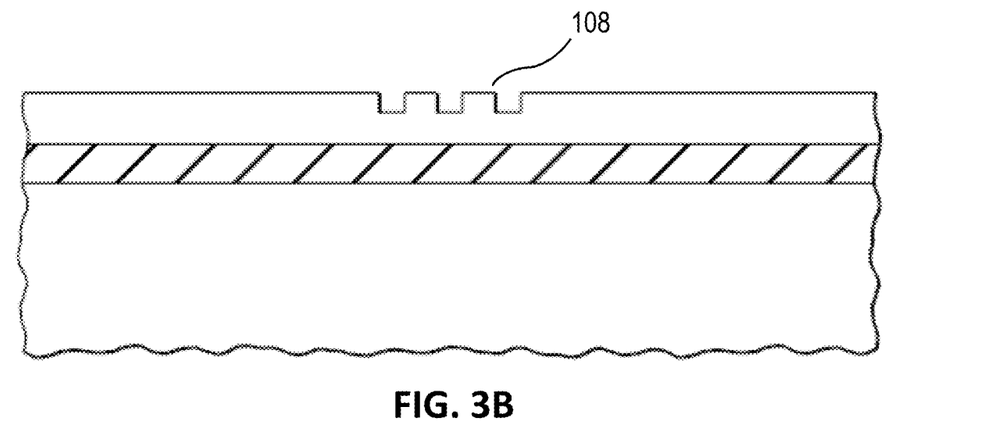
Figure 3C:
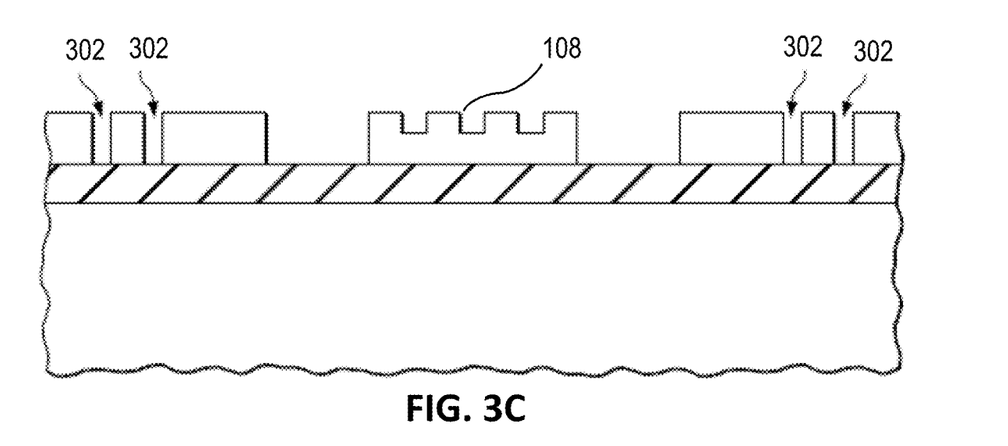

The process may begin at FIG. 3A with a substrate 120 such as a SOI wafer or other substrate. In the example depicted in FIG. 3A, two substrate layers 320 and 322 are shown separated by an oxide layer 330. The periodic dielectric structure 108 may be formed in various dielectric, micromachine-compatible materials including silicon nitride, silicon oxide, etc., and as a method of enhancement, it is not strictly limited to silicon and other types of semiconductors may be used. The device-layer thickness may set the height of the structure 132. Photolithography, including other lithography approaches, may be used to define the periodic dielectric structure 108 pattern in resist to serve as an etch mask for an inductively-coupled plasma reactive-ion etch (ICP-RIE) process or other suitable etch process. The etch transfers the pattern of the periodic dielectric structure 108 into the silicon device layer with a vertical side-wall profile as depicted in FIG. 3B. Following the pattern etch of periodic dielectric structure 108, a front side reactive ion-etch (RIE) or other etch to the oxide stop layer may be used to create the structure 132, or other beam-shaped structures. Additionally, the etch may incorporate anchors in preparation for parylene (or other material of channel 102) deposition. In some other examples, silicon nitride or silicon dioxide may be used to form a channel. Materials used as component materials may in some cases be replaced by other materials according to the desired properties of a particular particle positioning structure 100. Additionally, the example fabrication process depicted in FIG. 3 is but one example process that may be used to fabricate a particle positioning device 100 as depicted in FIG. 1.

Figure 3D:
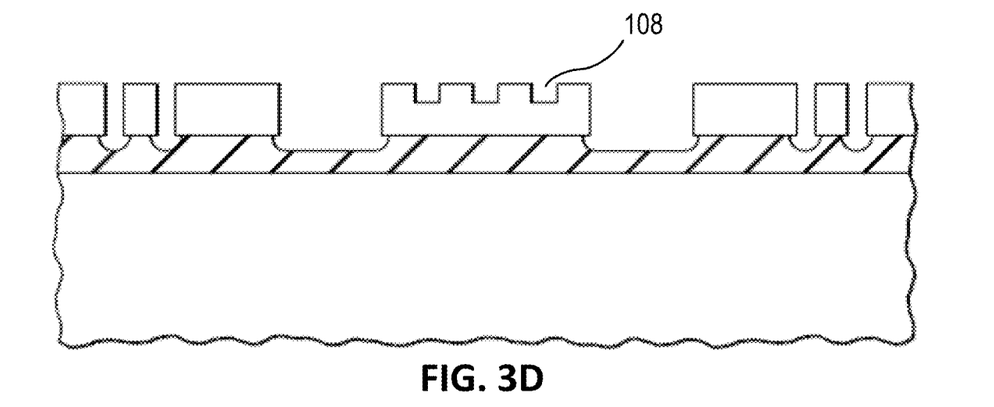

Parylene, and/or another material used to form channel 102, may be at least partially optically clear, demonstrating adequate transmission over most of the visible spectrum and well into the near-infrared, and accordingly may be effective to transmit light from light source 130 (depicted in FIG. 1). For example, parylene may be effective to transmit light from a Nd:YVO$_4$ laser. Parylene offers conformal, durable coatings from chemical-vapor deposition. Additionally, due to the durability of parylene, parylene may be used to create larger channels 102 which may be needed to accommodate larger particles (e.g., mammalian cells from 10-15 microns in diameter). However, the adhesion between parylene and other materials, including silicon, may be poor. To increase the strength of the fluidic channels 102 and pressure rating of fluidic channels 102, the fabrication process may employ mechanical anchors in the silicon device layer to ensure strong attachment of the parylene, which is important in determining the maximum fluidic pressure supported by the device as well as device reliability. Utilizing the under-layer oxide of the SOI wafer, a silicon RIE or other suitable etch technique may be used to create the anchor holes or trenches 302. A timed HF (hydrofluoric acid) etch or other suitable etch of the oxide layer may be used to create cavities to enhance anchoring as depicted in FIG. 3D.

Figure 3E:
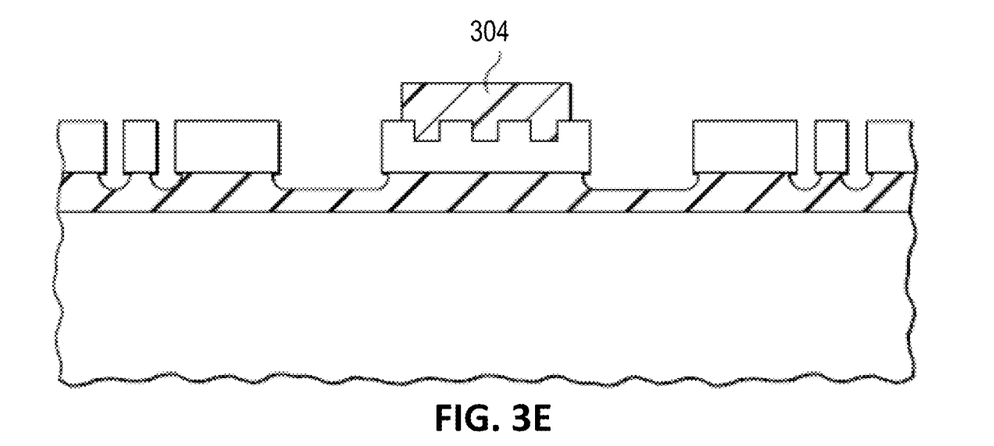
Figure 3F:
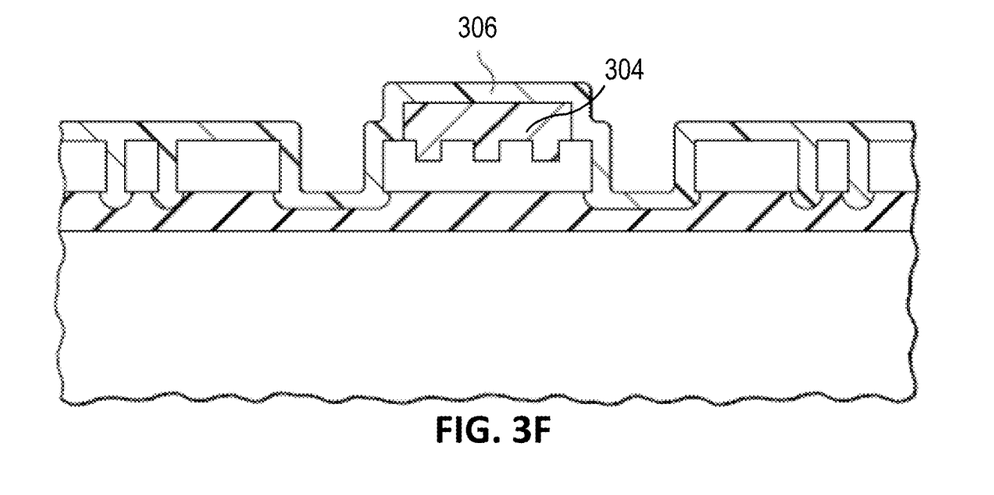

As depicted in FIG. 3E, patterned photoresist 304 may serve as the sacrificial layer to support parylene channel formation. In various other examples, patterned photoresist 304 may be applied prior to the oxide layer etch used to create cavities (depicted in FIG. 3D). In some examples, it may be beneficial to form patterned photoresist 304 prior to etching the oxide layer to create cavities, so that the photoresist material does not fill the cavities and thereby result in poor anchor sites for the parylene layer 306. Through standard photolithography processing, where a photoresist layer is spun onto the unreleased structure 102 with adequate thickness to accommodate device surface topology, optical patterning and subsequent development of the photoresist layer defines the on-chip fluidic network and determines the interior dimensions of the channel. The height of patterned photoresist 304 may be adjusted in order to adjust the height of the channel 102, adaptable to suit various application requirements, particle and cell types. Parylene layer 306 may be chemical-vapor deposited, encapsulating the beam-shaped resonator and the sacrificial photoresist, forming strong anchors in the SOI wafer as depicted in FIG. 3F.

Figure 3G:
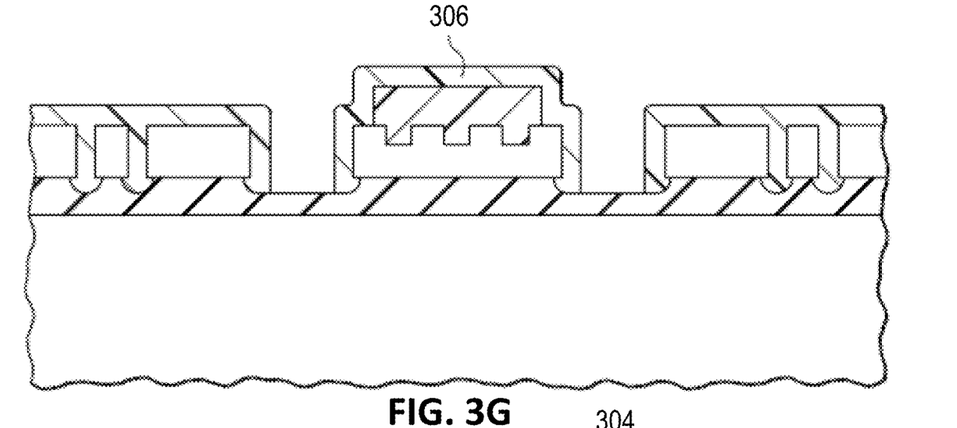
Figure 3H:
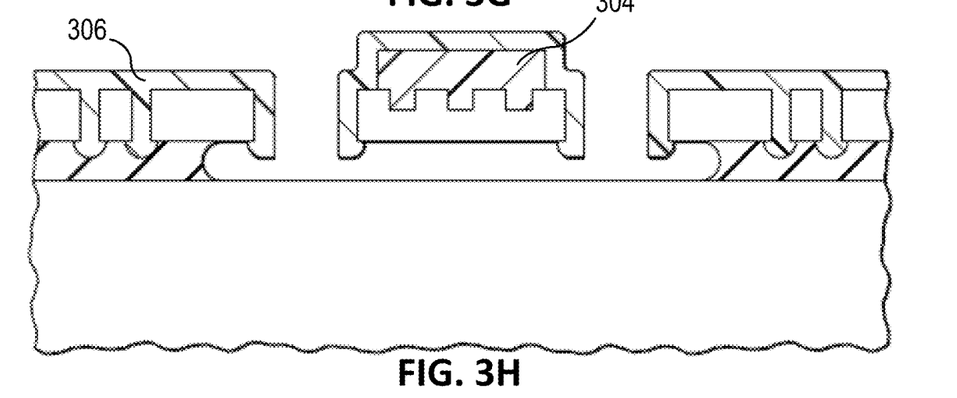
Figure 3I:
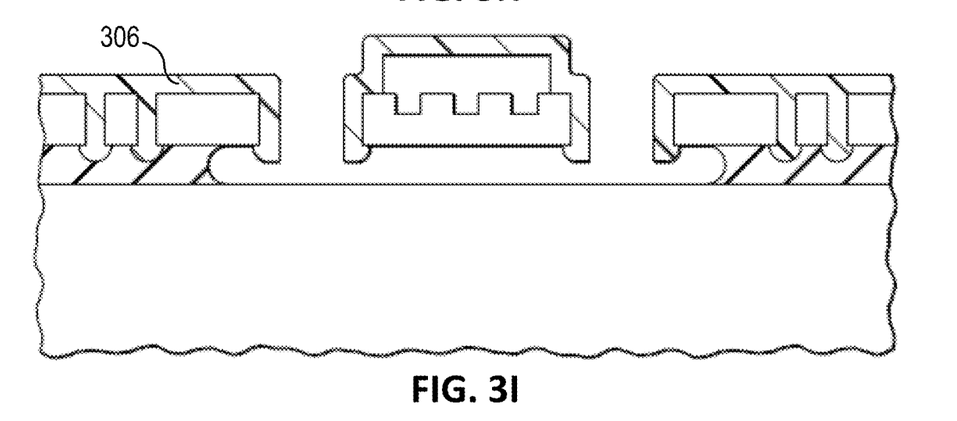
Figure 4A:
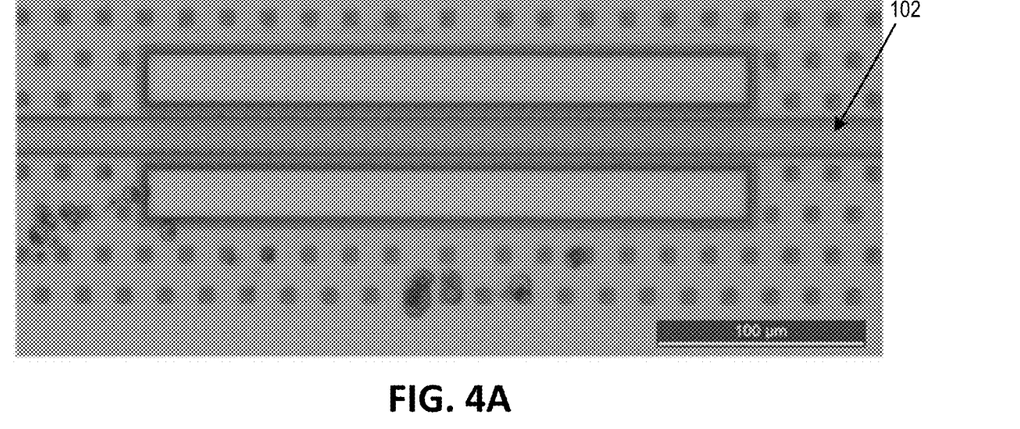
FIG. 4A depicts a fabricated device comprising a particle positioning structure, in accordance with various embodiments of the present disclosure.
Figure 4B:
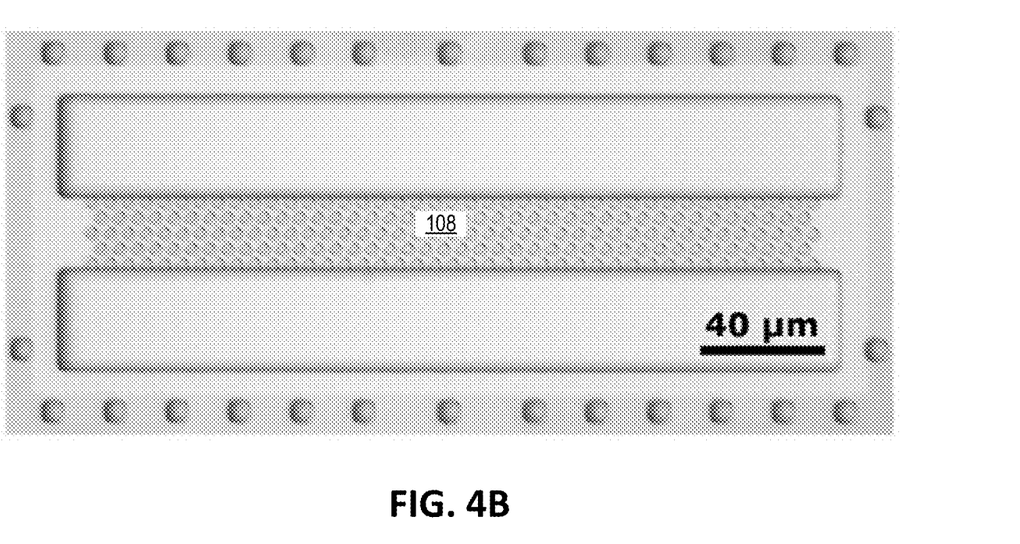
FIG. 4B depicts a fabricated device without a channel structure in order to show the underlying periodic dielectric structure, in accordance with various embodiments of the present disclosure.

As depicted in FIG. 3G, an oxygen ICP-RIE etch or other suitable etch may be used to open access through the parylene layer 306 to the exposed oxide and may be used to define ports (e.g., input ports and/or output ports) to the fluidic channel 102 (depicted in FIG. 1). In various other examples, the backside of substrate 322 (e.g., the side or surface of substrate 322 opposite of periodic dielectric structure 108) may be etched using oxide layer 330 as a stop underlayer. Additionally, in some examples, a second parylene layer may be deposited to enclose the interior of the channel and isolate the substrate. HF wet etching or other suitable etching may be used to fully release the structure as depicted in FIG. 3H. A solvent (e.g., acetone) release of the patterned photoresist 304, as depicted in FIG. 3I leaves freestanding, transparent fluidic channels atop the particle positioning structure 100 including an integrated periodic dielectric structure 108 and silicon structure 132. In various examples, particle positioning structure 100 may comprise a resonator that can be actuated by applying a voltage to front and back electrodes deposited on the device. FIG. 4A depicts a final fabricated device including particle positioning structure 100. FIG. 4B depicts a device without the channel 102 to show a clearer view of the underlying periodic dielectric structure 108.

As an alternative porting structure for more robust peripheral fluidic attachment, a deep reactive-ion etch (DRIE) can open ports in the backside of the wafer (not shown). The thick insulating oxide layer helps ensure the integrity of the ports (by managing the etch depth and thermal stress) during a backside etch and allows resist spinning on the front side port structures. The ports can be later opened in the final HF and solvent release. An additional parylene deposition may create a fully enclosed channel wall for possible isolation from substrate.

Figure 5:
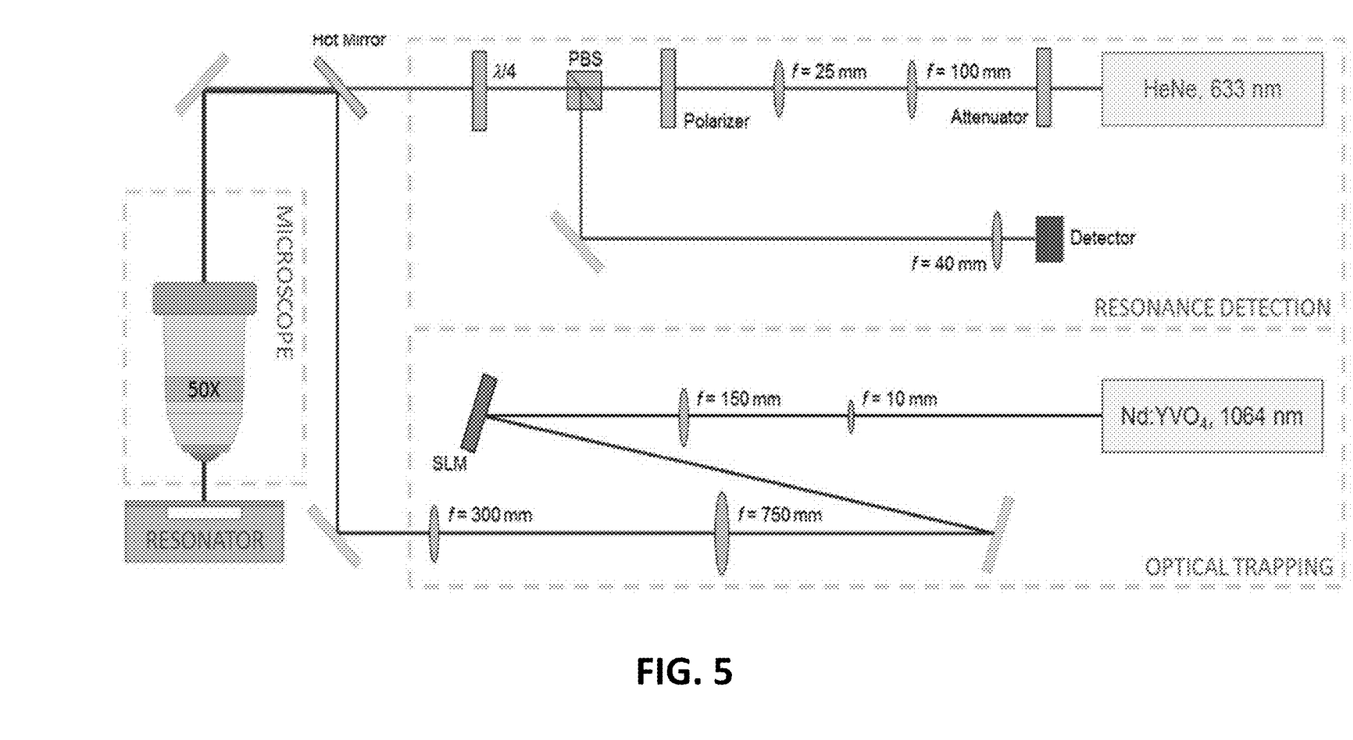
FIG. 5 depicts an example system using a particle positioning structure and a MEMS resonator for particle analysis, in accordance with various aspects of the present invention.

In example particle positioning structures 100 including MEMS resonators, two separate lasers may be used. A first laser may be used for optical trapping of particles while a second laser may be used for optical detection of the resonant frequency. FIG. 5 depicts an example system using a particle positioning structure 100 and a MEMS resonator for particle analysis.

As depicted in FIG. 5, a HeNe (35 mW, 633 nm) laser may be used for the purpose of optical detection of the resonant frequency. After attenuation and collimation, a linear polarizer, a quarter-waveplate ($\lambda/4$), and a polarizing beam splitter (PBS) may be used to maximize the intensity transmitted to the photodiode detector. The quarter-waveplate converts the laser's linear polarization to a circularly polarized beam. After undergoing reflection and propagation in the opposite direction, the handedness of circular polarization switches the output linear orientation maximizing light reflection at the PBS to optimize a signal to noise ratio of the detected output.

The Nd:YVO$_4$ laser (5 W, 1064 nm) or other near-infrared laser light source may enable optical trapping to manipulate cells and other particles within the channel 102 (FIG. 1) and adjacent to the periodic dielectric structure 108 (FIG. 1) to enhance measurement precision. A series of collimating and magnifying lenses may be used with a spatial light modulator to shape and size the trapping beam. The spatial light modulator can create holographic beam patterns at the focal plane of the microscope to allow for additional functionality and adaptability of the trapping approach. An optical illumination light source may be used to illuminate the channel and thereby provide a means for visual observation of particles within the channel using the microscope.

In various examples, the MEMS resonator may be operated with gain-controlled feedback using the optically detected signal and modifying its phase and gain to drive the resonator to its natural frequency using the resonator as the frequency determining element in a closed-loop oscillator system. This configuration can quickly respond to changing mass on the resonator while maintaining high fidelity and stability in the natural frequency measurement. Additionally, such a configuration does not require an external source.

Figure 6:
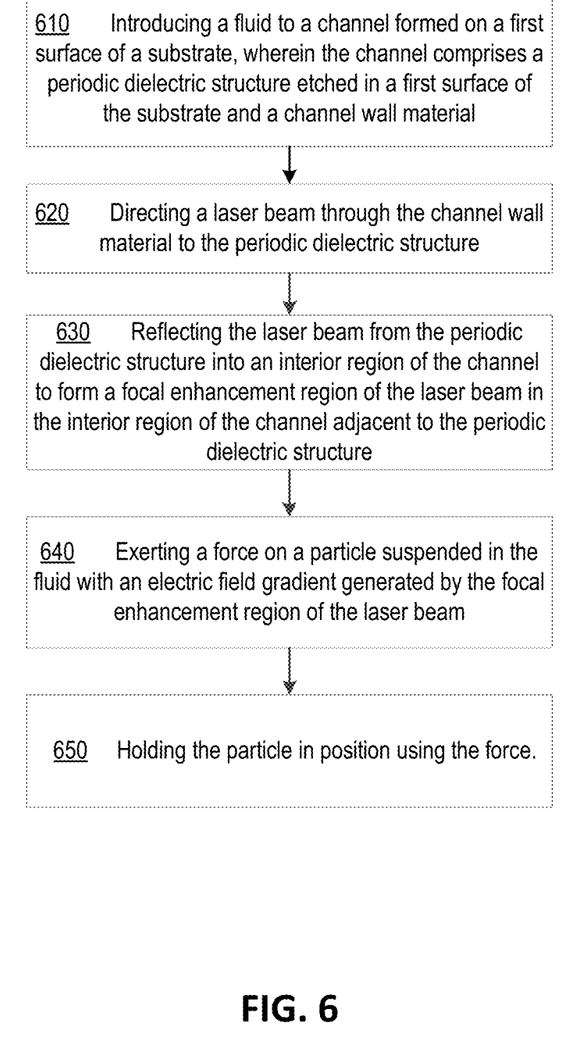
FIG. 6 depicts an example process for positioning a particle using optical trapping in a particle positioning structure, in accordance with various aspects of the present disclosure.

FIG. 6 depicts an example process for positioning a particle using optical trapping in a particle positioning structure 100, in accordance with various aspects of the present disclosure. Those portions of FIG. 6 that have been described previously with respect to FIGS. 1-5 may not be described again for purposes of clarity and brevity.

The process in FIG. 6 may begin at action 610, "Introducing a fluid to a channel formed on a first surface of a substrate". At action 610, a fluid may be introduced into a channel (e.g., channel 102 of FIG. 1). The channel may comprise a periodic dielectric structure (e.g., periodic dielectric structure 108) etched in a first surface of a substrate (e.g., substrate 120 depicted in FIG. 1) and a channel wall material (e.g., parylene or silicon nitride).

The process in FIG. 6 may continue from action 610 to action 620, "Directing a laser beam through the channel wall material to the periodic dielectric structure." At action 620, a laser beam (e.g., laser light 110 depicted in FIG. 1) may be directed through a wall of channel 102 to periodic dielectric structure 108, as depicted in FIG. 1.

The process in FIG. 6 may continue from action 620 to action 630, "Reflecting the laser beam from the periodic dielectric structure into an interior region of the channel to form a focal enhancement region of the laser beam in the interior region of the channel adjacent to the periodic dielectric." At action 630 the laser beam may be reflected by the periodic dielectric structure 108 into an interior region of the channel (e.g., channel 102). As depicted in FIG. 2, the periodic dielectric structure 108 may be effective to form a focal enhancement region (e.g., the beam waist depicted at focal plane 204) of the laser beam in the interior region of the channel.

The process in FIG. 6 may continue from action 630 to action 640, "Exerting a force on a particle suspended in the fluid with an electric field gradient generated by the focal enhancement region of the laser beam." At action 640, an optical force may be exerted on a particle. For example, a dielectric particle may be attracted to a region of strongest electric field produced by the focal enhancement region of the laser beam.

The process in FIG. 6 may continue from action 640 to action 650, "Holding the particle in position using the force." At action 650, the particle may be held in position using the optical trapping force produced by the focal enhancement region of the laser beam. In various examples, the particle may be a living cell. In some further examples, the particle may be held against a surface of the periodic dielectric structure 108 such that the particle resonates along with the particle positioning structure 100. In some further examples the particle may be sorted from among other particles using the optical trapping force.

Figure 7:
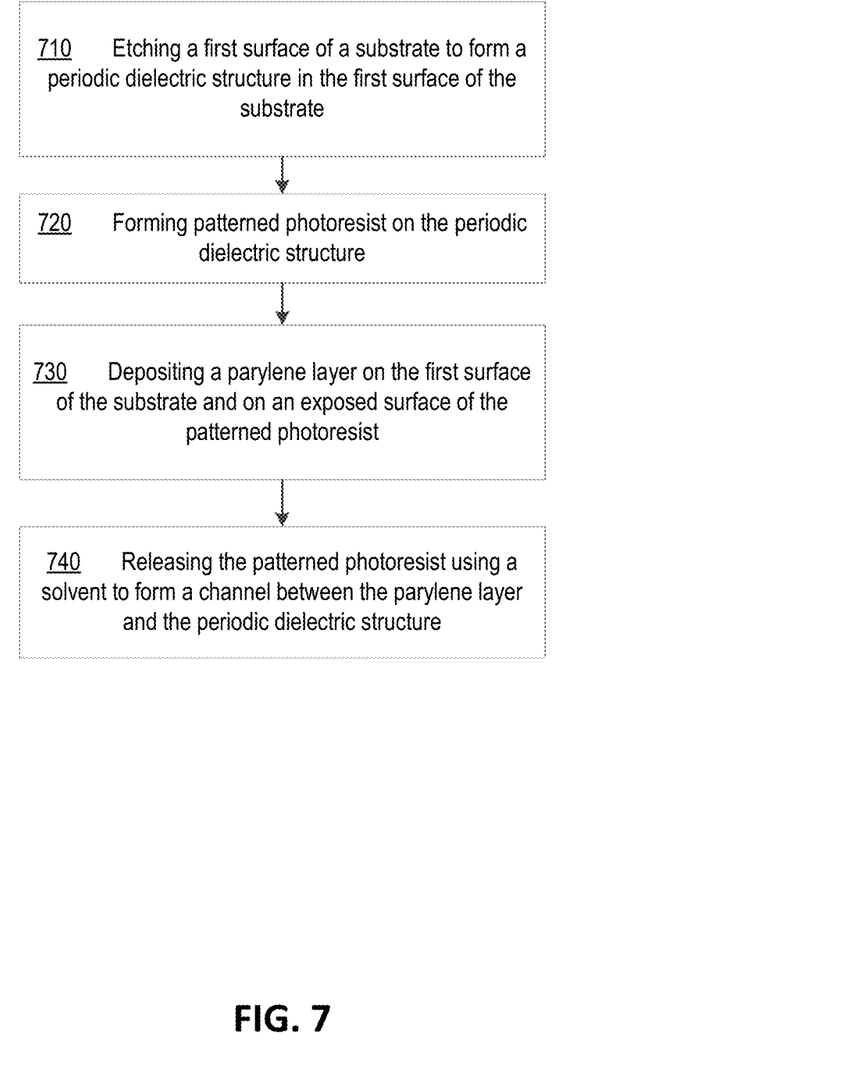
FIG. 7 depicts an example process for fabricating a particle positioning structure in accordance with various aspects of the present disclosure.

FIG. 7 depicts an example process for fabrication of a particle positioning structure 100, in accordance with various aspects of the present disclosure. Those portions of FIG. 7 that have been described previously with respect to FIGS. 1-6 may not be described again for purposes of clarity and brevity.

The process of FIG. 7 may begin at action 710, "Etching a first surface of a substrate to form a periodic dielectric structure in the first surface of the substrate." At action 710, the substrate material (e.g., a silicon wafer and or a silicon on insulator material) may be etched to form a periodic dielectric structure (e.g., periodic dielectric structure 108) etched into the surface of the substrate. In various examples, the particular pattern of the periodic dielectric structure may be designed according to properties of target particles (e.g., size of the particles). As described above, various parameters of the periodic dielectric structure may be adjusted in order to optimize the optical trapping mechanism of particle positioning device 100 for a particular particle.

The process depicted in FIG. 7 may continue from action 710 to action 720, "Coupling patterned photoresist to the periodic dielectric structure." At action 720, a sacrificial patterned photoresist may be patterned on the periodic dielectric structure. In some examples, the height of the patterned photoresist may determine the height of the channel of particle positioning structure 100.

The process depicted in FIG. 7 may continue from action 720 to action 730, "Depositing a parylene layer on the first surface of the substrate and on an exposed surface of the patterned photoresist." At action 730, a parylene layer may be deposited. The parylene layer may coat the exposed portions of the patterned photoresist as well as exposed portions of the substrate. In various examples, parylene may be deposited in a vapor phase. Further, in various examples, the parylene may adhere to the substrate using various anchors by depositing the parylene in one or more anchor holes/trenches and/or by allowing the parylene to at least partially coat portions of a lower side (in certain applications, even achieving full encapsulation) of the substrate opposite the patterned photoresist.

The process depicted in FIG. 7 may continue from action 730 to action 740, "Releasing the patterned photoresist using a solvent to form a channel between the parylene layer and the periodic dielectric structure." At action 740, a solvent (e.g., acetone or another solvent) may be used to release the channel (e.g., dissolve the patterned photoresist). Accordingly, the parylene layer may form a channel with the periodic dielectric structure forming a lower surface of the channel, as depicted in FIG. 3I.

Figure 8:
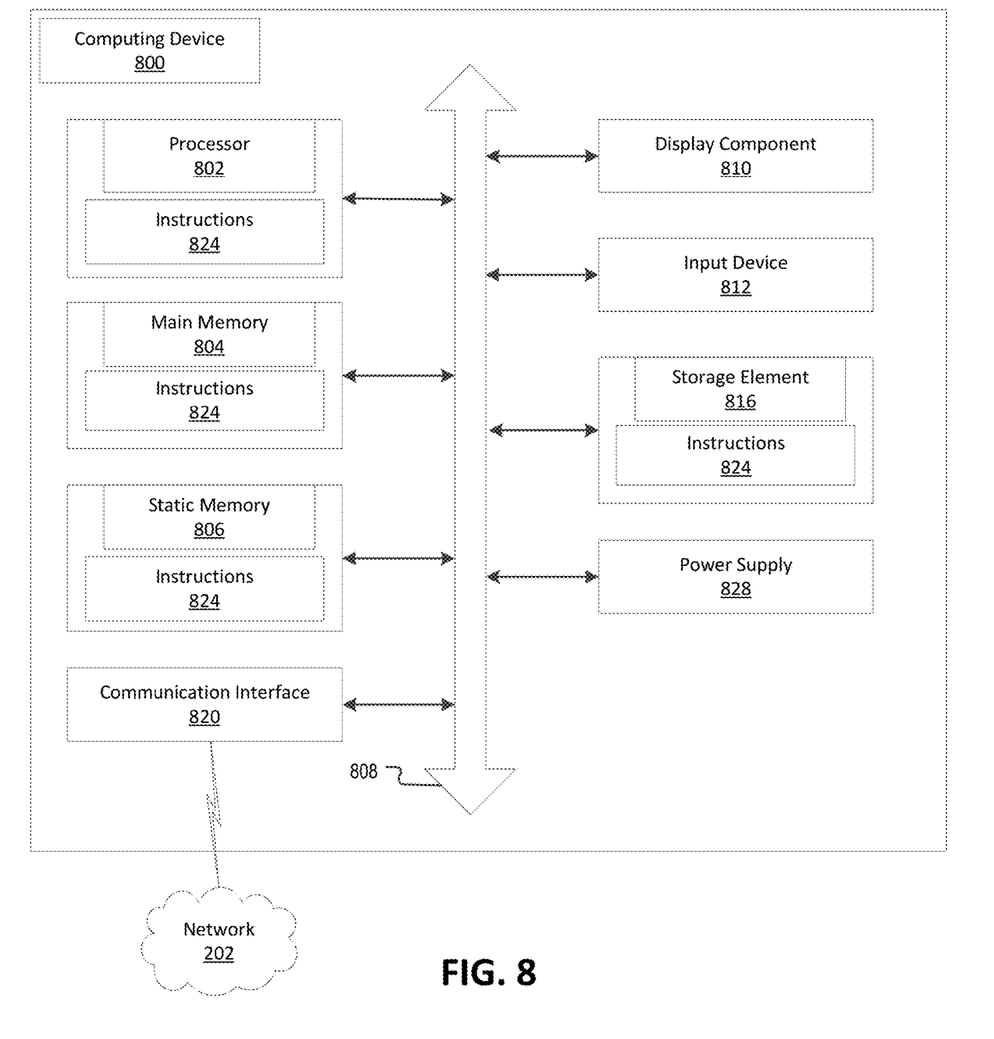
FIG. 8 depicts an example computing device effective to perform various techniques described herein.

Referring to FIG. 8, the block diagram illustrates components of a computing device 800, according to some example embodiments, able to read instructions 824 from a non-transitory machine-readable storage medium (e.g., a hard drive storage system) and perform any one or more of the methodologies discussed herein, in whole or in part. Specifically, FIG. 8 shows the computing device 800 in the example form of a computer system within which the instructions 824 (e.g., software, a program, an application, an applet, an app, or other executable code) for causing the computing device 800 to perform any one or more of the methodologies discussed herein may be executed, in whole or in part. For example, the computing device 800 may receive a signal generated by the photodiode detector depicted in FIG. 5. Additionally, the computing device 800 may be effective when determining the resonant frequency of a particle positioning device as described herein both before and after using optical trapping to hold a particle in position. In some examples, computing device 800 may be effective to determine mass, density, stiffness, and/or size of particles trapped using the optical trapping techniques described herein based on resonant frequencies of a particle positioning device actuated using a MEMS resonator. In some further examples, computing device 800 may be effective to control actuation of a MEMS resonator coupled to particle positioning structure 100. In some examples, the computing device 800 may be effective to perform various other particle analysis techniques in conjunction with the particle positioning structure 100 described herein.

In alternative embodiments, the computing device 800 operates as a standalone device or may be connected (e.g., networked) to other computing devices. In a networked deployment, the computing device 800 may operate in the capacity of a server computing device or a client computing device in a server-client network environment, or as a peer computing device in a distributed (e.g., peer-to-peer) network environment. The computing device 800 may include hardware, software, or combinations thereof, and may, as example, be a server computer, a client computer, a personal computer (PC), a tablet computer, a laptop computer, a netbook, a cellular telephone, a smartphone, a set-top box (STB), a personal digital assistant (PDA), a web appliance, a network router, a network switch, a network bridge, or any computing device capable of executing the instructions 824, sequentially or otherwise, that specify actions to be taken by that computing device. Further, while only a single computing device 800 is illustrated, the term "computing device" shall also be taken to include any collection of computing devices that individually or jointly execute the instructions 824 to perform all or part of any one or more of the methodologies discussed herein.

The computing device 800 includes a processor 802 (e.g., a central processing unit (CPU), a graphics processing unit (GPU), a digital signal processor (DSP), an application specific integrated circuit (ASIC), a radio-frequency integrated circuit (RFIC), or any suitable combination thereof), a main memory 804, and a static memory 806, which are configured to communicate with each other via a bus 808. The processor 802 may contain microcircuits that are configurable, temporarily or permanently, by some or all of the instructions 824 such that the processor 802 is configurable to perform any one or more of the methodologies described herein, in whole or in part. For example, a set of one or more microcircuits of the processor 802 may be configurable to execute one or more modules (e.g., software modules) described herein.

The computing device 800 may further include a display component 810. The display component 810 may comprise, for example, one or more devices such as cathode ray tubes (CRTs), liquid crystal display (LCD) screens, gas plasma-based flat panel displays, LCD projectors, or other types of display devices.

The computing device 800 may include one or more input devices 812 operable to receive inputs from a user. The input devices 812 can include, for example, a push button, touch pad, touch screen, wheel, joystick, keyboard, mouse, trackball, keypad, accelerometer, light gun, game controller, or any other such device or element whereby a user can provide inputs to the computing device 800. These input devices 812 may be physically incorporated into the computing device 800 or operably coupled to the computing device 800 via wired or wireless interface. For computing devices with touchscreen displays, the input devices 812 can include a touch sensor that operates in conjunction with the display component 810 to permit users to interact with the image displayed by the display component 810 using touch inputs (e.g., with a finger or stylus).

The computing device 800 may also include at least one communication interface 820, comprising one or more wireless components operable to communicate with one or more separate devices within a communication range of the particular wireless protocol. The wireless protocol can be any appropriate protocol used to enable devices to communicate wirelessly, such as Bluetooth, cellular, IEEE 802.11, or infrared communications protocols, such as an IrDA-compliant protocol. It should be understood that the communication interface 820 may also or alternatively comprise one or more wired communications interfaces for coupling and communicating with other devices.

The computing device 800 may also include a power supply 828, such as, for example, a rechargeable battery operable to be recharged through conventional plug-in approaches or through other approaches, such as capacitive charging. Alternatively, the power supply 828 may comprise a power supply unit which converts AC power from the power grid to regulated DC power for the internal components of the device 800.

The computing device 800 may also include a storage element 816. The storage element 816 includes the machine-readable medium on which are stored the instructions 824 embodying any one or more of the methodologies or functions described herein. The instructions 824 may also reside, completely or at least partially, within the main memory 804, within the processor 802 (e.g., within the processor's cache memory), or both, before or during execution thereof by the computing device 800. The instructions 824 may also reside in the static memory 806.

Accordingly, the main memory 804 and the processor 802 may also be considered machine-readable media (e.g., tangible and non-transitory machine-readable media). The instructions 824 may be transmitted or received over a network 202 via the communication interface 820. For example, the communication interface 820 may communicate the instructions 824 using any one or more transfer protocols (e.g., HTTP).

The computing device 800 may be implemented as any of a number of electronic devices, such as a tablet computing device, a smartphone, a media player, a portable gaming device, a portable digital assistant, a laptop computer, or a desktop computer. In some example embodiments, the computing device 800 may have one or more additional input components (e.g., sensors or gauges) (not shown). Examples of such input components include an image input component (e.g., one or more cameras), an audio input component (e.g., a microphone), a direction input component (e.g., a compass), a location input component (e.g., a GPS receiver), an orientation component (e.g., a gyroscope), a motion detection component (e.g., one or more accelerometers), an altitude detection component (e.g., an altimeter), and a gas detection component (e.g., a gas sensor). Inputs harvested by any one or more of these input components may be accessible and available for use by any of the modules described herein.

As used herein, the term "memory" refers to a non-transitory machine-readable medium capable of storing data temporarily or permanently and may be taken to include, but not be limited to, random-access memory (RAM), read-only memory (ROM), buffer memory, flash memory, and cache memory. The machine-readable medium is non-transitory in that it does not embody a propagating signal. While the machine-readable medium is described in example embodiments as a single medium, the term "machine-readable medium" should be taken to include a single medium or multiple media (e.g., a centralized or distributed database, or associated caches and servers) able to store instructions 824. The term "machine-readable medium" shall also be taken to include any medium, or combination of multiple media, that is capable of storing the instructions 824 for execution by the computing device 800, such that the instructions 824, when executed by one or more processors of the computing device 800 (e.g., processor 802), cause the computing device 800 to perform any one or more of the methodologies described herein, in whole or in part. Accordingly, a "machine-readable medium" refers to a single storage apparatus or device as well as cloud-based storage systems or storage networks that include multiple storage apparatus or devices. The term "machine-readable medium" shall accordingly be taken to include, but not be limited to, one or more tangible (e.g., non-transitory) data repositories in the form of a solid-state memory, an optical medium, a magnetic medium, or any suitable combination thereof.

While the invention has been described in terms of particular embodiments and illustrative figures, those of ordinary skill in the art will recognize that the invention is not limited to the embodiments or figures described. For example, in various embodiments described above, a parylene channel is described. However, in other embodiments, other materials may be used to form channel 102 described above in reference to FIG. 1.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show details of the invention in more detail than is necessary for the fundamental understanding of the invention, the description taken with the drawings and/or examples making apparent to those skilled in the art how the several forms of the invention may be embodied in practice.

As used herein and unless otherwise indicated, the terms "a" and "an" are taken to mean "one," "at least one" or "one or more." Unless otherwise required by context, singular terms used herein shall include pluralities and plural terms shall include the singular.

Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural and singular number, respectively. Additionally, the words "herein," "above," and "below" and words of similar import, when used in this application, shall refer to this application as a whole and not to any particular portions of the application.

The description of embodiments of the disclosure is not intended to be exhaustive or to limit the disclosure to the precise form disclosed. While specific embodiments and examples for the disclosure are described herein for illustrative purposes, various equivalent modifications are possible within the scope of the disclosure, as those skilled in the relevant art will recognize. Such modifications may include, but are not limited to, changes in the dimensions and/or the materials shown in the disclosed embodiments.

Specific elements of any embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

Therefore, it should be understood that the invention can be practiced with modification and alteration within the spirit and scope of the appended claims. The description is not intended to be exhaustive or to limit the invention to the precise form disclosed. It should be understood that the invention can be practiced with modification and alteration and that the invention be limited only by the claims and the equivalents thereof.

What is claimed is:

1. A system comprising:
a laser light source configured to emit a laser beam; and
a particle positioning structure, the particle positioning structure comprising:
   a substrate, wherein a first surface of the substrate comprises a periodic dielectric structure; and
   a channel wall material adhered to the substrate such that the channel wall material forms a freestanding channel adjacent to the periodic dielectric structure, wherein the channel wall material is at least partially optically transparent to the laser beam from the laser light source, wherein the substrate and the channel wall material are effective to be actuated at a resonant frequency;
wherein the laser light source is adapted to direct the laser beam through the channel wall material and through an interior region of the freestanding channel to the periodic dielectric structure, whereby the laser beam is reflected by the periodic dielectric structure into the interior region of the freestanding channel.

2. The system of claim 1, further comprising an optical illumination light source effective to illuminate a portion of the freestanding channel.

3. The system of claim 2, wherein the periodic dielectric structure is effective to at least partially focus the laser beam reflected by the periodic dielectric structure at a focal enhancement region, wherein the focal enhancement region is located in the interior region of the freestanding channel.

4. The system of claim 1, wherein the periodic dielectric structure comprises a plurality of divots etched in the first surface of the substrate in a periodic pattern.

5. The system of claim 1, wherein:
the periodic dielectric structure comprises a plurality of divots etched in the first surface of the substrate in a periodic pattern;
the periodic dielectric structure is effective to at least partially focus the laser beam reflected by the periodic dielectric structure at a focal enhancement region, wherein the focal enhancement region is located in the interior region of the freestanding channel; and
a position of the focal enhancement region is related to a depth of the plurality of divots.

6. The system of claim 1, wherein:
the periodic dielectric structure comprises a plurality of divots etched in the first surface of the substrate in a periodic pattern;
the periodic dielectric structure is effective to at least partially focus the laser beam reflected by the periodic dielectric structure at a focal enhancement region, wherein the focal enhancement region is located in the interior region of the freestanding channel; and
a position of the focal enhancement region is related to a periodicity of the plurality of divots.

7. The system of claim 1, wherein the substrate is formed in a cantilever structure, the system further comprising an electrode effective to induce resonant electrostatic actuation of the particle positioning structure.

8. The system of claim 7, wherein the laser light source comprises a Nd:YVO4 or near-infrared laser light source positioned outside of the freestanding channel and effective to emit the laser beam, the system further comprising:
a HeNe laser light source positioned outside of the freestanding channel, the HeNe laser light source effective to direct a second laser beam to the substrate; and
a photodiode detector effective to detect the second laser beam reflected from the substrate.

9. The system of claim 1, wherein the channel wall material comprises parylene.

10. The system of claim 9, the particle positioning structure further comprising two or more parylene anchors at least partially underlying the substrate effective to secure the freestanding channel to the substrate.

11. A particle positioning system comprising:
a laser light source; and
a particle positioning structure, comprising:
a substrate layer comprising a periodic dielectric structure etched in a first surface of the substrate layer; and
a channel wall material adhered to the substrate layer such that the channel wall material forms a freestanding channel adjacent to the periodic dielectric structure, wherein the channel wall material comprises parylene and is at least partially optically transparent to a laser beam from the laser light source, wherein the substrate layer and the channel wall material are effective to be actuated at a resonant frequency;
wherein the periodic dielectric structure is effective to reflect the laser beam into an interior region of the freestanding channel.

12. The system of claim 11, further comprising:
an optical illumination light source effective to illuminate at least a portion of the freestanding channel.

13. The system of claim 11, wherein the periodic dielectric structure is effective to at least partially focus the laser beam reflected by the periodic dielectric structure at a focal enhancement region, wherein the focal enhancement region is located in the interior region of the freestanding channel.

14. The system of claim 11, wherein the periodic dielectric structure comprises a plurality of divots etched in the first surface of the substrate layer in a periodic pattern.

15. The system of claim 11, wherein:
the periodic dielectric structure comprises a plurality of divots etched in the first surface of the substrate layer in a periodic pattern;
the periodic dielectric structure is effective to at least partially focus the laser beam reflected by the periodic dielectric structure at a focal enhancement region, wherein the focal enhancement region is located in the interior region of the freestanding channel; and
a position of the focal enhancement region is related to a depth of the plurality of divots.

16. The system of claim 11, wherein:
the periodic dielectric structure comprises a plurality of divots etched in the first surface of the substrate layer in a periodic pattern;
the periodic dielectric structure is effective to at least partially focus the laser beam reflected by the periodic dielectric structure at a focal enhancement region, wherein the focal enhancement region is located in the interior region of the freestanding channel; and
a position of the focal enhancement region is related to a periodicity of the plurality of divots.

17. The system of claim 11, wherein the substrate layer is formed in a cantilever structure, the system further comprising an electrode effective to induce resonant electrostatic actuation of the particle positioning structure.

18. The system of claim 11, further comprising:
the laser light source, wherein the laser light source comprises a Nd:YVO4 or near-infrared laser light source positioned outside of the freestanding channel and effective to emit the laser beam,
a HeNe laser light source positioned outside of the freestanding channel, the HeNe laser light source effective to direct a second laser beam to the substrate layer; and
a photodiode detector effective to detect the second laser beam reflected from the substrate layer.

19. The system of claim 11, the particle positioning structure further comprising two or more parylene anchors at least partially underlying the substrate layer and securing the freestanding channel to the substrate layer.

* * * * *